United States Patent

Marquis et al.

Patent Number: 4,661,272
Date of Patent: Apr. 28, 1987

[54] THIOETHER DIESTER LUBRICATING OIL COMPOSITION

[75] Inventors: Edward T. Marquis; Lewis W. Watts, Jr.; Ernest L. Yeakey, all of Austin, Tex.

[73] Assignee: Texaco Inc., White Plains, N.Y.

[21] Appl. No.: 506,733

[22] Filed: Jun. 22, 1983

[51] Int. Cl.$^4$ .......................... C10M 157/06
[52] U.S. Cl. .................. 252/32.7 E; 252/33.4; 252/48.6; 252/50; 252/52 R
[58] Field of Search .............. 560/195; 252/32.7 E, 252/48.6

[56] References Cited

U.S. PATENT DOCUMENTS

| | | | |
|---|---|---|---|
| 2,460,436 | 2/1949 | Shoemaker et al. | 560/195 |
| 2,782,229 | 2/1957 | Dazzi | 560/195 |
| 4,009,211 | 2/1977 | Onopchenko et al. | 568/45 |
| 4,102,932 | 7/1978 | Onopchenko et al. | 568/45 |
| 4,253,980 | 3/1981 | Hammond et al. | 546/283 X |
| 4,306,070 | 12/1981 | Hammond et al. | 546/283 |
| 4,411,808 | 10/1983 | Gutierrez et al. | 252/48.6 |

FOREIGN PATENT DOCUMENTS 309007 9/1971 U.S.S.R. .............. 560/195

OTHER PUBLICATIONS

Hawley, G. G. ed, *The Condensed Chemical Dictionary*, Eighth Edition, Van Nostrand Reinhold Company, N.Y., 1971, p. 28.

*Primary Examiner*—Natalie Trousof
*Assistant Examiner*—Patricia M. Scott
*Attorney, Agent, or Firm*—Robert A. Kulason; Jack H. Park; Richard A. Morgan

[57] ABSTRACT

Provided is a novel thioether diester synthetic lubricating oil composition represented by the formula:

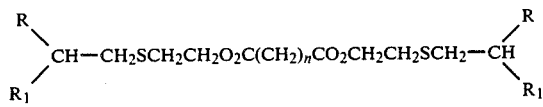

in which R and $R_1$ each represent alkyl radicals having from 1 to 6 carbon atoms, with the total number of carbon atoms in R, R, $R_1$, and $R_1$ ranging from about 6 to 20, and n is an integer from 2 to 5.

1 Claim, No Drawings

THIOETHER DIESTER LUBRICATING OIL COMPOSITION

BACKGROUND OF THE INVENTION

In great demand today are functional fluids which exhibit a high viscosity index and a low pour point, properties which are especially valuable in the lubricating oil field.

It has been found, however, that most functional fluids which exhibit a high viscosity index are still not fully suitable for use, for they fail to also exhibit a low pour point. Both properties are necessary if the functional fluid is to function in a wide range of operating environments.

It is an object of the invention to provide a novel thioether diester composition which exhibits properties which are desired in a functional fluid, viz., a low pour point and a high viscosity index.

DISCLOSURE INFORMATION STATEMENT

U.S. Pat. No. 4,009,211 and 4,102,932 disclose beta, beta-dialkylethylmercaptoethoxylates prepared by reacting a vinylidene olefin with mercaptoethanol to form an intermediate thioether ethanol adduct which is then reacted with ethylene oxide to form a beta-beta-dialkylethylmercaptoethoxylate; these additives are useful as a detergent for polyester fabrics.

SUMMARY OF THE INVENTION

The novel thioether diester compound of the invention is represented by the formula:

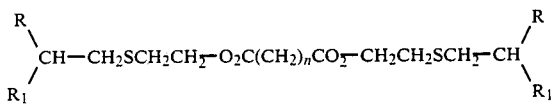

in which R and $R_1$ each represent an alkyl radical having from 1 to 12 carbon atoms, with the total number of carbon atoms in R, R, $R_1$, and $R_1$ ranging from about 6 to 40, and n is an integer from 2 to 10.

The thioether diester compound of the invention is prepared by reacting a vinylidene olefin with mercaptoethanol to form a thioether ethanol intermediate which is then reacted with a dicarboxylic acid to form the prescribed thioether diester compound.

DETAILED DESCRIPTION OF THE INVENTION

More specifically, the novel thioether diester compound of the invention is represented by the prescribed formula in which R and $R_1$ each represent a monovalent hydrocarbon or an alkyl radical having from 1 to 12 carbon atoms, with the total number of carbon atoms in R, R, $R_1$, and $R_1$ ranging from 6 to 40, and n is an integer from 2 to 10. The preferred thioether diester compound is one in which R and $R_1$ are alkyl radicals having from 1 to 4 carbon atoms and the total number of carbon atoms in R, R, $R_1$, and $R_1$ ranges from 8 to 14. Particularly preferred are compounds in which R is a methyl group, $R_1$ is an alkyl radical having from 2 to 4 carbon atoms and n is an integer from 3 to 4.

The novel compound of the instant invention is prepared in a two-step reaction process involving a first reaction between a vinylidene olefin defined herein below and mercaptoethanol to produce an intermediate reaction product and a second reaction between the intermediate product and a dicarboxylic acid to form the product of the invention.

The vinylidene olefin reactant that is employed is represented by the following structural formula:

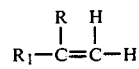

wherein R and $R_1$ are alkyl radicals having from 1 to 12 carbon atoms. A preferred vinylidene olefin is one in which R and $R_1$ are alkyl radicals having from 1 to 4 carbon atoms. A particularly preferred vinylidene olefin reactant is one in which one of the alkyl radicals is a methyl group.

Specific examples of vinylidene olefins that can be used include: 2-methyl-1-pentene, 2 propyl-1-pentene, 2-butyl-1-pentene, 2-ethyl-1-butene, and the like. The preferred vinylidene olefin employed is 2-methyl-1-pentene.

The dicarboxylic acid that is employed is represented by reference to the following structual formula:

wherein n is an integer from 2 to 10.

Specific examples of dicarboxylic acids that can be used include: succinic, glutaric and adipic acid. The preferred dicarboxylic acid is adipic acid.

In forming the adduct the vinylidene olefin and the mercaptoethanol are brought together and, while being stirred, maintained at a temperature of about 10° to 100° C. or higher, preferably about 50° to 80° C., a pressure of about 1 to 5 atmospheres, preferably about 1 atmosphere, for a reaction period of about 1 to 30 hours, preferably about 5 to 20 hours.

Solvents are not needed for adduct formation. However, to solubilize solid olefin feeds, solvents, such as methanol, ethanol, benzene, carbon tetrachloride, chloroform, carbon disulfide, can be present. Also, as the action readily occurs in air alone, initiators are not needed. However, initiators such as azobisisobutyronitrile, hydrogen peroxide, tert-butyl hydrogen peroxide, cumene hydroperoxide, ultraviolet light, and ozone, can be present.

Equimolar amounts of reactant olefin and mercaptoalcohol are theoretically required to form the adduct, that is, the intermediate reaction product. In practice, however, excess amounts of one of the reactants is used. When mercaptoethanol and a lower vinylidene olefin reactant, for example, $C_{10}$ olefin, are reacted, excess olefin is used, since the excess olefin can readily be removed from the adduct product by flash evaporation. When higher olefins are reacted with mercaptoethanol, excess mercaptoethanol is generally used, because the excess mercaptoethanol can be removed easily from the adduct merely by washing the same with water.

The adduct so obtained is then reacted with the dicarboxylic acid in an adduct to acid ratio of about 2:1. A catalyst, such as sulfuric acid, methylsulfonic acid, p-toluenesulfonic acid or any other suitable acid catalyst, may be employed to facilitate the esterfication reaction. The reaction mixture is maintained at a temperature of about 120° to 250° C., preferably about 120° to 200° C., a pressure of about 1 to 5 atmospheres, preferably about 1 atmosphere, for a reaction period of about 1 to 30 hours, preferably about 5 to 25 hours.

The invention defined herein can be further illustrated by the following:

EXAMPLE I

A. 174.0 grams (2.0 moles) of 2-methyl-1-pentene (C$_6$ vinylidene olefin) and 170.0 gram (2.18 moles) of mercaptoethanol are dissolved in 50 milliliters of isopropanol. This mixture is heated to 65° C. in the presence of air under atmospheric pressure and maintained under these conditions for about 18 hours. Gas chromatographic analysis of the flashed reaction product indicated a 83.5% yield of the thioether ethanol, which product is represented by the formula:

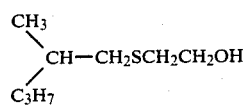

B. To the thioether ethanol reaction product produced in A. above is added 50 milliliters of p-toluenesulfonic acid, 50 milliliters of toluene, and 172.8 grams (1.2 moles) of adipic acid. The mixture is heated under atmospheric pressure to a temperature ranging up to about 197° C. and maintained under these conditions for approximately 20 hours. After distillation of the solvent, 45.3 weight percent yield of the diester of adipic acid and thioether ethanol, as determined by gas chromatographic analysis, is recovered, which product is represented by the formula:

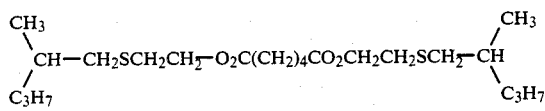

The viscosity index and pour point properties of the diester of adipic acid and thioether ethanol were compared against those of two other compounds: the first is a related diester formed from an alpha olefin, and the second is a hydrocarbon of similar molecular weight. The results are outlined below in Table I:

TABLE I

| Physical Properties | | | |
|---|---|---|---|
| | C$_6$—vinylidene olefin based adipate ester[1] | C$_6$—alpha olefin based adipate ester[2] | Typical C$_{30}$—hydrocarbon[3] |
| Viscosity Index | 165 | 166 | 120 |
| Pour Point | −50° F. | 50-60° F. | −50° F. |
| TGA at 233° C.[4] | 95.0 | 95.0 | 87.8 |

[1] Produced as described in Example II.
[2] Produced as described in Example II, except that a C$_6$ alpha olefin was substituted for the C$_6$ vinylidene olefin in preparing the end product of Example I.
[3] A mixture comprising straight and branched chained saturated hydrocarbons.
[4] In this test, the thermal gravimetric analysis (TGA) is determined by subjecting the product sample to 10° C./min. heating and expressing as a weight percentage the amount of sample remaining at 233° C.

From the data presented in Table I, it is evident that the C$_6$ vinylidene olefin based adipate ester has a surprisingly low pour point as compared to a C$_6$ alpha olefin based adipate ester, namely, −50° F. as compared to 50°-60° F. It is also evident that the C$_6$-vinylidene olefin based ester demonstrates substantially superior viscosity index and TGA values over the C$_{30}$-hydrocarbon fluid. Thus, because the novel composition of this example exhibits a high viscosity index and a low pour point, it has significant utility as a lubricant composition.

EXAMPLE 2

A diester of succinic acid is prepared following the procedure of Example 1, except that succinic acid is substituted for adipic acid. The diester of succinic acid and thioether ethanol is represented by the formula:

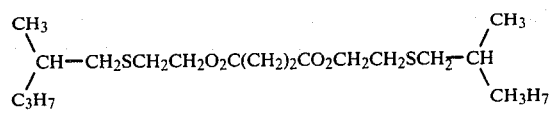

EXAMPLE 3

A diester of glutaric acid is prepared following the procedure of Example 1, except that glutaric acid is substituted for adipic acid and 2-propyl-1-pentene is substituted for 2-methyl-1-pentene. The diester of glutaric acid and thioether ethanol is represented by the formula:

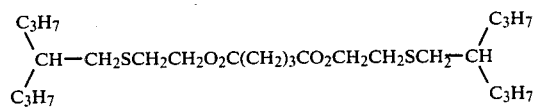

The novel composition of the invention is useful neat as a motor oil or crankcase lubricant. Alternatively, it may be mixed with a mineral oil to form a mixed base lubricating oil composition. The composition of the invention can be employed as a lubricant for spark ignited and compression ignited internal combustion engines, including automobile and truck engines, two cylinder engines, and the like. It is also useful in gas engines, stationary power plant engines and turbines.

Whether it is used neat or in admixture with a mineral lubricating oil conventional additives can be added thereto including dispersants, such as alkenylsuccinimides, overbased calcium sulfonates, polyethoxylated alkylphenols, zinc dialkyldithiophosphates, diarylamines, and polymethacrylate V.I. improvers, olefin copolymer V.I. improvers and silicon antifoamants.

We claim:
1. A lubricating oil composition comprising
   a. a mixed base consisting essentially of
      (1) a mineral oil
      (2) a thioether diester compound represented by the formula:

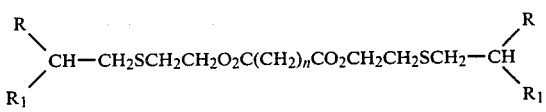

in which R and R$_1$ each represent an alkyl radical having from 1 to 12 carbon atoms, with the total number of carbon atoms in R, R, R$_1$ and R$_1$ ranging from about 6 to 40, and n is an integer from 2 to 10, and
   b. one or more additives selected from the group consisting of dispersants, overbased calcium sulfonates, polyethoxylated alkylphenols, zinc dialkyldithiophosphates, diarylamines, polymethacrylate V.I. improvers, olefin copolymer VI improvers and silicone antifoamants.

* * * * *